US006936746B2

United States Patent
Effing et al.

(10) Patent No.: US 6,936,746 B2
(45) Date of Patent: Aug. 30, 2005

(54) POLYELECTROLYTE SOLID SYSTEM, METHOD FOR THE PRODUCTION THEREOF AND A WOUND DRESSING

(75) Inventors: Jochen Effing, Turnhout (BE); Bernd Riedel, Unterwellenborn (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 10/182,341

(22) PCT Filed: Jan. 25, 2001

(86) PCT No.: PCT/EP01/00785

§ 371 (c)(1),
(2), (4) Date: Oct. 7, 2002

(87) PCT Pub. No.: WO01/55486

PCT Pub. Date: Aug. 2, 2001

(65) Prior Publication Data

US 2003/0163073 A1 Aug. 28, 2003

(30) Foreign Application Priority Data

Jan. 27, 2000 (DE) ........................................ 100 03 397

(51) Int. Cl.⁷ ................................................ A61F 13/00
(52) U.S. Cl. .............................. 602/48; 602/41; 602/42
(58) Field of Search .............. 602/41–59; 604/304–308, 604/367, 374, 379, 3, 376, 368; 424/443–449

(56) References Cited

U.S. PATENT DOCUMENTS 3,546,142 A 12/1970 Michaels et al.
5,173,521 A 12/1992 Ishino
6,602,994 B1 * 8/2003 Cash et al. .................... 536/30

FOREIGN PATENT DOCUMENTS

| CA | 2208496 | 12/1997 | |
|----|---------|---------|---|
| DE | 198 41 404 | 9/1998 | |
| DE | 19741063 C1 * | 8/1999 | .............. C08J/5/22 |
| EP | 0 199 531 | 10/1986 | |
| EP | 0 430 491 | 6/1991 | |
| JP | 49099675 A * | 9/1974 | |
| WO | WO 00/12144 | 3/2000 | |

OTHER PUBLICATIONS

B. Riedel et al.; *Novel Polyanion–Polycation–Microfibride Blend Nonwoven Based on Cellulose Derivatives*; vol. 49; Mar. 1999; Chemical Fibers International; pp. 55–57.

* cited by examiner

Primary Examiner—Kim M. Lewis
(74) Attorney, Agent, or Firm—Young & Basile, P.C.

(57) ABSTRACT

A polyelectrolyte solid system, especially provided in the form of flocks, flock composites, nonwovens of paper, comprised of a mixture of fibrous entities containing polyanion-polycation complexes and entities containing polyanions and/or containing polycations. A method for producing a polyelectrolyte solid system, whereby for the production of the mixture of the fibrous entities containing polyanion-polycation complexes and of the entities containing polyanions and/or containing polycations are used as aqueous solvents of polyanionic and polycationic polyelectrolytes. A wound dressing produced by using a polyelectrolyte solid system.

20 Claims, 2 Drawing Sheets

POLYELECTROLYTE SOLID SYSTEM, METHOD FOR THE PRODUCTION THEREOF AND A WOUND DRESSING

BACKGROUND

The invention is a polyelectrolyte solid system, a method for its production and a wound dressing.

Based on their high content of covalently bonded salt groups, polyelectrolytes (PTE) possess the ability to absorb large quantities of water and in so doing to go into solution. In many applications, particularly in the area of treating wounds, pediatric care and incontinence materials, where it is a matter of binding secreted water, or aqueous secretions, it is necessary to maintain the integrity of the absorber used so that it can be removed in a mechanically stable form. To ensure this, the otherwise water-soluble polyelectrolytes are crosslinked in many different ways by means of intermediate bonds, by covalent or ionic bonds to the extent that, upon the entry of water, solvation occurs only to the stage of highly swollen gels.

Since absorbers of this kind on a polyelectrolyte base are hard and brittle because of their high salt content and their crosslinking in the solid state, they are embedded in flexible polymers, specifically in cellulose or in polyurethane, in order to obtain good workability and to fixate them against being flushed out.

This is the description given by the Beiersdorf Company to a polyurethane foam under the commercial name "Cultinova", in which extremely fine superabsorbent particles of partially crosslinked polyelectrolyte powders are dispersed.

This flexible material, when introduced into a physiological sodium chloride solution, is able to absorb substantial quantities of water and to act as an absorbent coating for moist wound management.

Furthermore it is known, using the viscose method, to process Na-carboxymethyl cellulose as a polyelectrolyte (PEL) together with cellulose into highly swellable viscose fibers. The fixation of the intrinsically water-soluble Na-carboxymethyl cellulose in the viscose fibers is achieved by the formation of non-water-soluble intermolecular hydrogen bridge bonds between the macromolecules of the cellulose and those of the Na-carboxymethyl cellulose. The disadvantage here is that the polyelectrolytes have to be embedded in a second flexible polymer.

Furthermore a process is described in EP 0 616 630 in which highly swellable filaments containing polyelectrolytes can be produced expensively and therefore disadvantageously by partial chemical conversion of cellulose fibers, specifically of lycoell fibers.

Ionically crosslinked polyelectrolytes, specifically ionically highly crosslinked polyelectrolyte complexes, also known as polyanion-polycation complexes, have been used only to a small extent until now for the production of absorbent materials, in spite of their easy accessibility. Polyelectrolyte complexes result from the reaction of anionic and cationic macromolecules (polyelectrolytes) and are crosslinked to each other ionically through a plurality of salt groups. They are soluble in complex systems of solutions, specifically saline solutions (JP 49099651), formic acid (JP 62183768) or water/HCl/dioxane (JP 49010232). Membranes can be produced from these solutions which, as described in U.S. Pat. No. 3,546,142 and U.S. Pat. No. 3,549,016, are suitable for ultrafiltration in aqueous solutions. The macromolecules are arranged without structure in an indifferent random orientation in these polyelectrolyte complex membranes.

In contrast, the polyelectrolyte complex membranes which, according to DD 160 393 and DD 218 734/A4, are created on the contact surfaces of solutions of anionic and cationic polyelectrolytes are distinguished by an advantageous bi-layer structure. However, these polyelectrolyte complex membranes are very thin and consequently cannot sustain mechanical loads. They are proposed primarily for encapsulating biologically active materials (DD 215 795 A1), in addition to ultrafiltration (DD 200 471/3; DD 152 287).

DE 197 41 063 describes planar entities in the form of paper, nonwoven material, woven material or laminate, which are produced from a mixture of fine fibers which are soluble in water or highly swellable anionic and cationic polyelectrolyte fibers and/or fibrins and/or spherical particles. The final structure of these materials does not form unit after water or aqueous solutions and/or aqueous emulsions and/or aqueous suspensions have acted on them through the polyelectrolyte complex membranes resulting on the contact surfaces between the polyanionic and polycationic components. The disadvantage here is that the oppositely charged fibers, fibrins or spherical particles are only ionically crosslinked at points and on the surface and consequently the resulting gel demonstrates inadequate mechanical stability.

Furthermore, in the last two decades great progress has been made in the treatment of dermal wounds, such as burns, operating wounds, ulcers. The so-called "hydroactive wound dressings" have become increasingly important. These dressings make it possible to keep the wounds moist and at the same time to absorb excess secretions, to inhibit the entry of external bacteria and to perform a non-traumatic change of the dressing because they do not adhere to the wound.

For the initial phases of healing, when cleaning is performed and secretions are present, wound coatings of this type are generally desirable, which can be conformed to the base of the wound, or easily tamponed into deeper wounds, which possess high secretion absorption capability by forming a gel and in the swollen state have adequate consistency so that they can be removed from the wound in a single or a few pieces. In later phases of healing, wound coverings which release moisture to the wound and prevent it from drying out are often beneficial.

The greatest importance in practice today attaches to applications based on hydrocolloids, hydrogels and fiber dressings from aligns.

Hydrocolloid compounds are compounds in which hydrocolloids (water-absorbent particles or polymers based on polyelectrolytes) are dispersed in an elastomer matrix. They possess great absorbency for secretions and are self-adhesive. The disadvantage is their lack of suitability for tamponage into deeper or jagged wounds, as well as their tendency to partially disintegrate under high absorption of secretions, thus increasing the time spent cleaning when changing dressings. Their application in the case of infected wounds is problematic because of the semi-occlusivity of the dressings.

The use of hydrogels as wound dressings is restricted to wounds with medium or low rates of secretion as a result of their restricted capacity to absorb secretions. Many of the gels are characterized by severe liquefaction so that they have to be removed from the wound by intensive rinsing when the dressing is changed.

These materials satisfy the performance criteria described above only to a limited extent, since they either lose their stability under heavy absorption of secretions or liquify, tamponment is difficult and they find only restricted use in the case of infected wounds.

SUMMARY

It is desirable to prepare a polyelectrolyte solid material system, or a method for the production of the same, which possesses adequate mechanical stability. In addition, a wound dressing should be prepared which consists of a tamponage-capable material having high absorbent capability, which in a swollen condition possesses high internal cohesion so that the wound covering can be removed from the wound in one or a few pieces when the dressing is changed, whereby healing of the wound is actively supported.

BRIEF DESCRIPTION OF THE DRAWING

The various features of the present invention are shown in the following drawing in which.

DETAILED DESCRIPTION

In the present invention, it was discovered that polyelectrolyte solid material system specifically in the form of flocks, flock composites, nonwovens or paper, which consists of a mixture of fibrous entities containing polyanion-polycation complexes and entities containing polyanion and/or polycation, does not exhibit the prior disadvantages, but swells to form mechanically stable gels upon the entry of water or aqueous solutions, such as a 0.9% sodium chloride solution or aqueous secretions, while preserving its integrity. Under the effects of water the entities crosslink with each other by means of ionic bonds, and the result is the formation of highly swollen, mechanically stable gels. Because of their suctioning and gel-forming properties the materials can be used in multiple ways, for example, as wound coverings, medicinal implants or deposits, in cosmetics as moisture dispensers, as carrier material for cell cultures and as protective layers, sealing materials or as binders.

Figure 2:
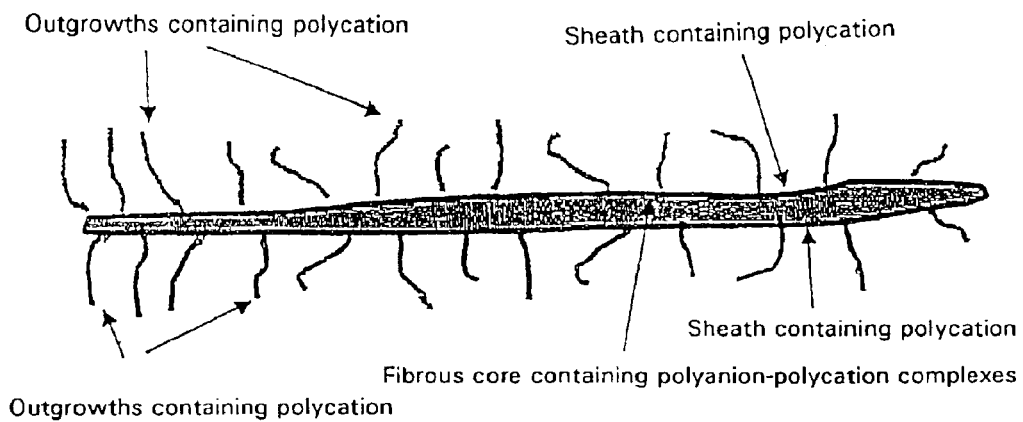
FIG. 2 is a schematic representation depicting one aspect of the structure of the present invention.

One feature of the inventive polyelectrolyte solid material systems are the fibrous entities containing polyanion-polycation complexes. An entity of this kind contains in addition to the ionically crosslinked core, or block, other polyanionic and/or polycationic components. The fibrous entities, morphologically classifiable among the fibrins, containing polyanion-polycation complexes can demonstrate the schematically represented structure shown in FIG. 2.

Figure 3:
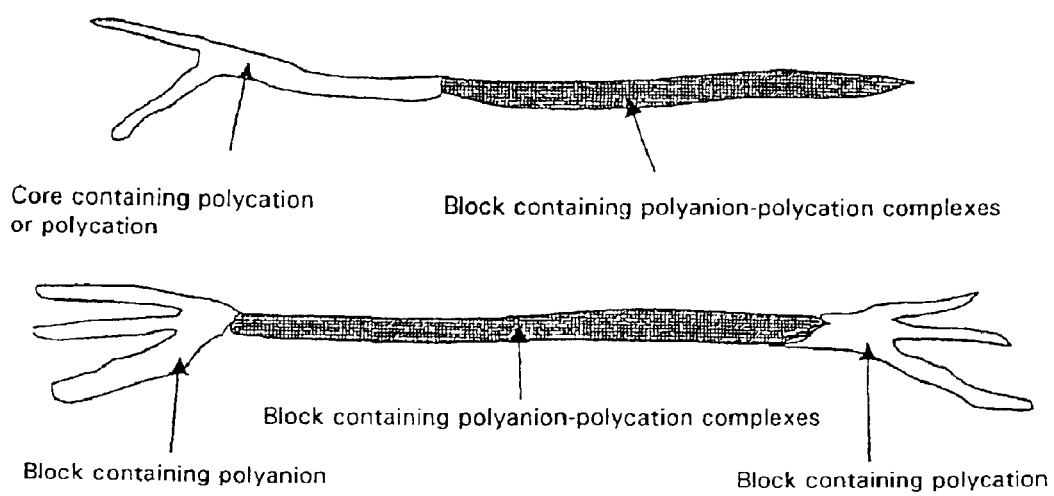
FIG. 3 is a schematic diagram of another aspect of the structure of the present invention.

They can also have the block structure shown in FIG. 3.

The fibrous entities containing polyanion-polycation complexes represent reinforcing materials which, upon the entry of water or of aqueous solutions, or of aqueous secretions respectively, are ionically crosslinked with each other and/or with fibrous entities containing polyanion and/or polycation, which are similarly contained together with the polyelectrolyte solid material system, by means of the polyanionic and polycationic components solidly fixated on their surface. Through their presence they give the gel resulting from solvation of the entities containing polyanion and/or polycation the necessary mechanical strength to preserve its integrity.

All water-soluble anionic and cationic PEL, whose polymer chains consist of at least 10 monomer blocks are suitable for the production of the polyelectrolyte solid material systems. Water-soluble salts of carboxymethyl cellulose and/or polyacrylic acid and/or polymethacrylic acid and/or pectin and/or carboxymethyl chitosan are preferably used as anionic PEL, and as cationic PEL preferably water-soluble chitosan salts.

The ratio of the polyanionic and the polycationic components in the mixture of the fibrous entities containing polyanion-polycation complexes and the entities containing polyanion and/or polycation can deviate up to 98%, preferably up to 80% from the stoichiometric polyanion/polycation ratio.

In a special aspect, the mixtures of fibrous entities containing polyanion-polycation complexes and the entities containing polyanion and/or polycation are fixated on or in carriers.

In an advantageous aspect of the invention the mixtures of the fibrous entities containing polyanion-polycation complexes and of the entities containing polyanion and/or polycation contain additional ingredients, preferably fillers and non-ionic active ingredients which are not involved in the polyanion-polycation reaction.

It is furthermore advantageous if the fibrous entities containing polyanion-polycation complexes and the entities containing polyanion and/or polycation contain low- and high-molecular ingredients such as silver salts or active ingredients having ionic groups or gelatins which are bonded through salt bonds to one or more entities containing polyanion-polycation complexes and entities containing polyanion and/or polycation.

It is furthermore advantageous if the distribution of the entities containing polyanion-polycation complexes and of the entities containing polyanion and/or polycation is not homogeneous in the flocks, flock compounds, nonwovens or paper formed from the inventive polyelectrolyte solid systems, but if it is created intentionally, preferably in layers.

The invention further relates to a process for producing a polyelectrolyte solid material system. Primarily aqueous solutions of polyanionic and polycationic PEL are used for the production of the polyelectrolyte solid material systems under the invention, consisting of mixtures of fibrous entities containing polyanion-polycation complexes and entities containing polyanion and/or polycation. At a suitable temperature these solutions can be transported through pipes by applying pressure and squeezed through nozzles. To obtain homogeneous solutions, it is advantageous in some bases to peptize preferably powdered PEL in a water-miscible PEL non-solvent and to use this dispersion to produce the solution. Substances of a type which are used as precipitants in the production of mixtures of fibrous entities containing polyanion-polycation complexes and of entities containing polyanion and/or polycation are preferably used as the non-solvent. It can furthermore be advantageous if the dissolving process is terminated prematurely and the resulting aqueous solutions still contain undissolved PEL particles or PEL gel particles. It can similarly be advantageous to start with the insoluble acid or base form of the PEL and to bring it into solution through the addition of suitable bases or acids.

The prerequisite for the creation of the entities containing polyanion-polycation complexes shown schematically in the preceding figures is the joint passage of the initial PEL solution through a mixing tube, where the anionic and the cationic PEL react with one another to form a polyanion-polycation complex film. With the static and/or dynamic mixing elements located if necessary in the mixing tube, the size of the boundary surface and thus the content of polyanion-polycation complex film can be fundamentally influenced.

The production of the mixtures of fibrous entities containing polyanion-polycation complexes and entities containing polyanion and/or polycation is carried out by mechanical spinning of the premixed solutions of anionic and cationic polyelectrolytes containing complex polyanion-polycation film using hydrophilic precipitants in an intensive shear field. High-shear mixers working on the rotor-stator principle are preferably used as shear field generators. In mechanical spinning, fibrous entities containing exclusively polyanion are formed from the polyanion solution, fibrous entities containing exclusively polycation are formed from the polycation solution and the fibrous entities containing polyanion-polycation complexes are formed from the polyanion-polyanion-polycation complex film as well as from the polyanion and polycation solutions adhering thereto. The fibrous entities leave the shear field generator dispersed in the precipitant.

The polyanion-to-polycation ratio as well as the turbulence in the mixing tube can be selected such that during the mechanical spinning only fibrous entities containing exclusively polyanion or exclusively polycation are created in addition to the fibrous entities containing polyanion-polycation complexes.

During the mechanical spinning process most of the water passes from the PEL solutions into the precipitant. In order to prevent the entities from melting together during the drying process as a result of the partial dissolving of the PEL, the residual water in and around the fibrous entities is carefully removed by azeotropic distillation. The hydrophilic precipitant contains at least one component which forms an azeotrope with the water.

Finally, the invention relates to a wound dressing in which a polyelectrolyte solid material system as previously described finds an application. Provision can be made for the dressings to be available in the form of powders, strips for tamponage or flat compresses.

Specifically the dressings can have a water content of from 0 to 20% by weight, specifically from 0.5 to 5% by weight.

In the case of a wound dressing in the form of flat compresses, the polyelectrolyte solid systems can be applied to carrier materials. Alternatively, the polyelectrolyte solid systems can be laminated between two or more carried materials. The carrier materials in question can be films, textiles, plastic films, nonwoven materials, paper or foams.

The invention shall be explained in greater detail using four examples:

EXAMPLE 1:

In a beaker 100 grams of powdered carboxymethyl cellulose/sodium salt medium viscosity from the Fluka Company are added in small amounts to 900 grams of water and stirred vigorously until a clear high-viscosity solution (Solution A) has formed. In a second beaker 450 grams of water and 50 grams of chitosan low viscosity from the Fluka Company are ground into a loose paste using an Ultraturax and homogenized. While being stirred, 10% hydrochloric acid is slowly added until the chitosan has bone into solution (Solution B) as chitosan hydrochloride. The volume of HCl added is to be measured so that the pH value of the resulting solution is 5.5.

Figure 1:
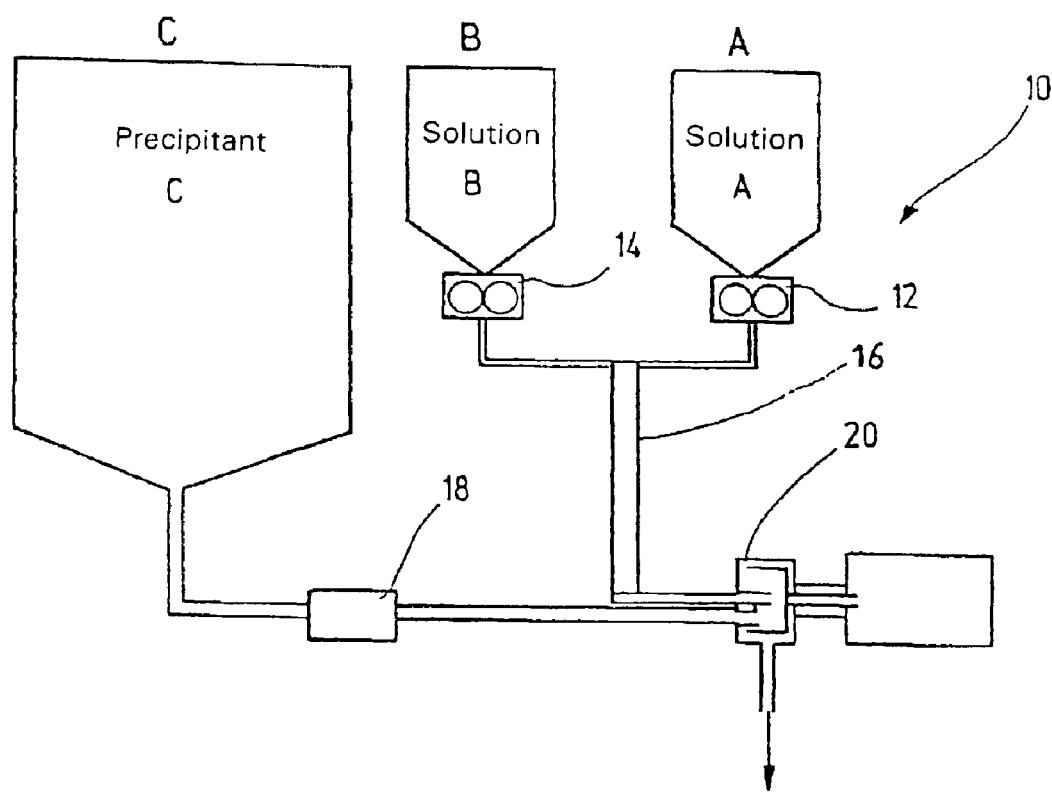
FIG. 1 is a pictorial representation of an apparatus for carrying out the process of the present invention.

Solution A and Solution B are spun together in the apparatus 10 sketched in FIG. 1 into fibrous entities containing polyanion-polycation complexes and entities containing polyanion and polycation.

To achieve this, Solution A and Solution B are put into containers A and B and fed via separate gear pumps 12, 14 in a ratio of 2:1 and with a throughput of 60 g/min to the mixing tube 16, through which they pass forming polyanion-polycation complex boundary surface films. The resulting mixture in the mixing tube 16 is brought simultaneously with 340 g/min of a 2:1 n-propanol/acetone mixture, which is kept in the precipitant container C and metered by a membrane pump 18, into the rotation center of the spinning head 20 (Ultraturax UTL 25 from the IKA Company) and spun mechanically at a speed of 24,000 rpm. 400 grams of PEL dispersion leave the shear field generator per minute.

The dispersion of the fibrous entities is drawn off in 200-gram amounts through a Buchner funnel provided with a filter paper (diameter 100 mm) and the n-propanol/acetone/water mixture still adhering to the filter cake is removed at 60° C. in an explosion-proof drying chamber equipped with an exhaust.

The nonwovens obtained in this fashion absorb more than ten times their weight of a 0.9% sodium chloride solution and in this state they are flexible and can withstand mechanical loads.

EXAMPLE 2:
a) production of a dispersion of fibrous entities in accordance with Example 1
b) production of a dispersion of fibrous entities in accordance with Example 1, but the ratio of the solutions of carboxymethyl cellulose-sodium and chitosan hydrochloride brought for spinning is 1:9.

To form a nonwoven, first 20 grams of the dispersion of fibrous PEL entities produced in accordance with B is drawn off by means of a Buchner funnel (diameter 100 mm) furnished with a filter paper and then 810 grams of the dispersion of fibrous PEL entities produced in accordance with a) is carefully poured on and similarly drawn off. The removal of the still adhering propanol/acetone/water mixture is carried out as in Example 1. The result is double-layer nonwovens which absorb more than ten times their weight of 0.9% sodium chloride solution and in this condition are flexible and can withstand mechanical loads.

EXAMPLE 3:

In a beaker 895 grams of water and 5 grams of cellulose are beaten with an Ultraturax and ground into a very fine dispersion. Then 50 grams of powdered carboxymethyl cellulose-sodium salt of high viscosity from the Fluka Company are reduced to a slurry in 50 grams of a 2:1 mixture of n-propanol and acetone and the resulting dispersion is added to the cellulose dispersion while being stirred vigorously. It is stirred until a high-viscosity cellulose dispersion (Solution A) has formed. In a second beaker 475 grams of water and 25 grams of chitosan high viscosity from the Fluka Company are ground into a fine paste using an Ultraturax and homogenized. While being stirred, 10% hydrochloric acid is added until the chitosan has gone into solution (Solution B) as chitosan hydrochloride. The quantity of HCl added is to be measured such that the pH value of the resulting solution is 5.5.

The production of the PEL dispersion and its processing is carried out as in Example 1. In this way nonwovens can be produced in which cellulose support fibers are contained, in addition to the fibrous entities containing polyanion-polycation complexes and entities containing polycation and/or polycation. After swelling in 0.9% sodium chloride solution, the resulting is a flexible and mechanically strong gel composite.

EXAMPLE 4:

The nonwovens produced in Example 1 are shredded into flocks using an MF 10 impact crusher basic sieve hole size 2 mm from IKA. 0.5 grams of these flocks are poured into a 2×2 cm mold and lightly compressed into a loose flock composite which can absorb more than ten times its weight of a 0.9% sodium chloride solution and in this state is flexible and can sustain mechanical loads.

What is claimed is:

1. A polyelectrolyte solid material system specifically in the form of one of flocks, flock composites, nonwovens or paper, characterized in that the polyelectrolyte solid material system consists of a mixture of fibrous entities containing polyanion-polycation complexes and entities containing one of polyanion and polycation.

2. The polyelectrolyte solid material system of claim 1, wherein the entities containing the polyanion includes at least one of carboxymethyl cellulose, polyacrylic acid, polymethacrylic acid, pectin and carboxymethyl chitosan acting as anionic water soluble salts and the entities containing the polycation includes at least one cationic polyelectrolyte, the cationic polyelectrolyte including water-soluble chitosan salts.

3. The polyelectrolyte solid material system of claim 1, wherein the ratio of polyanionic and polycationic components in the mixture of fibrous entities containing polyanion-polycation complexes and of entities containing polyanion or polycation diverges up to 98% from the stoichiometric polyanion-polycation ratio.

4. The polyelectrolyte solid material system of claim 1, wherein the mixtures of the fibrous entities consisting of polyanion-polycation complexes and of the entities containing one of polyanion and polycation are fixated in and, on carriers.

5. The polyelectrolyte solid material system of claim 1, wherein the mixture of fibrous entities consisting of polyanion-polycation complexes and of the entities containing one of polyanion and polycationic contains additional components which are not part of the polyanion-polycation reaction.

6. The polyelectrolyte solid material system of claim 5, wherein at least one of the components not part of the polyanion-polycation reaction represent fibers for mechanically reinforcing the system.

7. The polyelectrolyte solid material system of claim 1, wherein the mixture of the fibrous entities containing polyanion-polycation complexes and of the entities containing one of polyanion and polycation contains low-molecular and high-molecular components which are bound by salt bonds to at least one entity containing polyanion-polycation complexes and to at least one entity containing one of polyanion and polycation.

8. The polyelectrolyte solid material system from one of the preceding claims, wherein the distribution of the entities consisting of polyanion-polycation complexes and of the entities containing polyanion and polycation is not homogenous, but specifically a stratified distribution exists.

9. A process for producing a polyelectrolyte solid material system of claim 1, comprising the step of producing a mixture of the fibrous entities containing polyanion-polycation complexes using aqueous solutions of polyanionic and polycationic polyelectrolytes.

10. The process of claim 9, wherein the production step comprises introducing a joint flow of aqueous solutions of anionic and cationic polyelectrolytes through a mixing tube.

11. The process of claim 10, wherein one of static and dynamic mixing elements are located in the mixing tube.

12. The process according to claim 10 wherein the mixing of fibrous entities containing polyanion-polycation complexes and entities containing one of polyanion and polycation take place by mechanical spinning of premixed aqueous solutions of anionic and cationic polyelectrolytes with the use of hydrophilic precipitants.

13. The process for producing a polyelectrolyte solid material system according to claim 12 wherein the hydrophilic precipitants contain at least one component which forms an azeotrope with water.

14. A wound dressing, comprising a polyelectrolyte solid material system according to claim 1.

15. The wound dressing of claim 14, wherein the dressings comprise the form of one of powders, strips for tamponage and flat compresses.

16. The wound dressing of claim 14, wherein the dressings comprise a water content of 0 to 20 percent by weight.

17. The wound dressing of claim 14, wherein the polyelectrolyte solid material system is applied to carrier materials.

18. The wound dressing from claim 17, wherein the carrier materials comprise at least one of films, textiles, plastic sheets, nonwoven materials, paper and foams.

19. The wound dressing of claim 14 formed of flat compresses, wherein the polyelectrolyte solid material system is laminated between at least two carrier materials.

20. The polyelectrolyte solid material system of claim 1, wherein the entities containing polyanion include at least one anionic polyelectrolyte, wherein the anionic polyelectrolyte is selected from the group consisting of water soluble salts of carboxymethyl cellulose, polyacrylic acid pectin, or carboxylmethyl chitosan and the entities containing polycation include at least one cationic polyelectrolyte, wherein the cationic polyelectrolyte is selected from the group consisting of water soluble chitosan salts.

* * * * *